(12) United States Patent
Treado et al.

(10) Patent No.: US 9,329,086 B2
(45) Date of Patent: *May 3, 2016

(54) SYSTEM AND METHOD FOR ASSESSING TISSUE OXYGENATION USING A CONFORMAL FILTER

(71) Applicant: CHEMIMAGE TECHNOLOGIES LLC, Pittsburgh, PA (US)

(72) Inventors: Patrick J. Treado, Pittsburgh, PA (US); Ryan Priore, Wexford, PA (US)

(73) Assignee: ChemImage Technologies LLC, Pittsburgh, PA (US)

( * ) Notice: Subject to any disclaimer, the term of this patent is extended or adjusted under 35 U.S.C. 154(b) by 60 days.

This patent is subject to a terminal disclaimer.

(21) Appl. No.: 13/905,817

(22) Filed: May 30, 2013

(65) Prior Publication Data

US 2013/0321813 A1 Dec. 5, 2013

Related U.S. Application Data

(63) Continuation-in-part of application No. 13/734,024, filed on Jan. 4, 2013, now Pat. No. 9,041,932.

(60) Provisional application No. 61/652,898, filed on May 30, 2012.

(51) Int. Cl.
*G01N 21/00* (2006.01)
*G01J 3/51* (2006.01)
(Continued)

(52) U.S. Cl.
CPC ............... *G01J 3/51* (2013.01); *G01J 3/0224* (2013.01); *G01J 3/0272* (2013.01); *G01J 3/457* (2013.01);
(Continued)

(58) Field of Classification Search
CPC .............. G01J 3/32; G01J 3/36; G01J 3/51; G01J 3/457; G01N 21/255
USPC ............ 356/301, 432–440, 416, 364–369, 39
See application file for complete search history.

(56) References Cited

U.S. PATENT DOCUMENTS

| 6,234,250 B1 | 5/2001 | Green |
| 6,588,505 B2 | 7/2003 | Beck |

(Continued)

FOREIGN PATENT DOCUMENTS

| AU | 2009354176 | 9/2012 |
| CA | 2654763 | 3/2011 |

(Continued)

OTHER PUBLICATIONS

The Future of "Malovent Intent" Detection, http://www.wired.co.uk/magazine/archive/2010/07/start/automated-malevolent-intent-detection, last accessed Aug. 26, 2013.

(Continued)

*Primary Examiner* — Hoa Pham
(74) *Attorney, Agent, or Firm* — Pepper Hamilton LLP

(57) ABSTRACT

A portable system and method for analyzing biological tissue samples and detecting analytes associated with tissue oxygenation using a conformal filter. A conformal filter, which may comprise a tunable filter, is configured to filter interacted photons conforming to a spectral shape correlated with an analyte of interest. Conformal filter configurations may be selected by consulting a modified look-up table associated with an analyte. An iterative methodology may be used to calibrate a conformal design for an analyte of interest, refine a previous conformal filter design for an analyte of interest, and/or generate a new conformal filter design for an analyte of interest.

44 Claims, 12 Drawing Sheets

(51) Int. Cl.
- *G01J 3/457* (2006.01)
- *G01N 21/25* (2006.01)
- *G01J 3/02* (2006.01)
- *G01N 21/33* (2006.01)
- *G01N 21/359* (2014.01)
- *G01N 21/65* (2006.01)
- *G01N 21/71* (2006.01)
- *G01J 3/12* (2006.01)
- *G01N 21/64* (2006.01)
- *G01N 21/35* (2014.01)

(52) U.S. Cl.
CPC ....... *G01N 21/255* (2013.01); *G01J 2003/1213* (2013.01); *G01N 21/33* (2013.01); *G01N 21/35* (2013.01); *G01N 21/359* (2013.01); *G01N 21/65* (2013.01); *G01N 21/718* (2013.01); *G01N 2021/6471* (2013.01); *G01N 2201/0221* (2013.01); *G01N 2201/067* (2013.01); *G01N 2201/129* (2013.01)

(56) References Cited

U.S. PATENT DOCUMENTS

| | | |
|---|---|---|
| 6,604,581 B2 | 8/2003 | Moake |
| 6,640,130 B1 | 10/2003 | Freeman |
| 6,640,132 B1 | 10/2003 | Freeman |
| 6,741,884 B1 | 5/2004 | Freeman |
| 6,810,279 B2 | 10/2004 | Mansfield |
| 6,937,885 B1 | 8/2005 | Lewis |
| 7,013,172 B2 | 3/2006 | Mansfield |
| 7,150,324 B2 | 12/2006 | Laursen |
| 7,428,045 B2 * | 9/2008 | Stewart et al. ............... 356/301 |
| 7,623,233 B2 | 11/2009 | Freese |
| 7,697,141 B2 | 4/2010 | Jones |
| 7,911,605 B2 | 3/2011 | Myrick |
| 7,920,258 B2 | 4/2011 | Myrick |
| 8,027,855 B2 | 9/2011 | Freese |
| 8,049,881 B2 | 11/2011 | Myrick |
| 8,154,726 B2 | 4/2012 | Blackburn |
| 8,175,688 B2 | 5/2012 | Lewis |
| 8,184,295 B2 | 5/2012 | Myrick |
| 8,208,147 B2 | 6/2012 | Myrick |
| 8,212,216 B2 | 7/2012 | Perkins |
| 8,213,006 B2 | 7/2012 | Myrick |
| 8,213,012 B2 | 7/2012 | Myrick |
| 8,224,425 B2 | 7/2012 | Freeman |
| 8,237,920 B2 | 8/2012 | Jones |
| 8,237,929 B2 | 8/2012 | Myrick |
| 8,240,189 B2 | 8/2012 | Myrick |
| 8,283,633 B2 | 10/2012 | Myrick |
| 8,320,996 B2 | 11/2012 | Panasyuk |
| 8,345,234 B2 | 1/2013 | Myrick |
| 8,352,205 B2 | 1/2013 | Myrick |
| 8,358,418 B2 | 1/2013 | Myrick |
| 8,374,682 B2 | 2/2013 | Freeman |
| 8,379,199 B2 | 2/2013 | Freese et al. |
| 8,395,769 B2 * | 3/2013 | Stewart et al. ............... 356/301 |
| 8,400,637 B2 | 3/2013 | Myrick |
| 8,406,859 B2 | 3/2013 | Zuzak |
| 8,463,366 B2 | 6/2013 | Freeman |
| 2001/0013410 A1 | 8/2001 | Beck |
| 2001/0013411 A1 | 8/2001 | Beck |
| 2001/0042617 A1 | 11/2001 | Beck |
| 2001/0043146 A1 | 11/2001 | Beck |
| 2003/0192689 A1 | 10/2003 | Moake |
| 2004/0065475 A1 | 4/2004 | Laursen |
| 2007/0038042 A1 | 2/2007 | Freeman |
| 2007/0294094 A1 | 12/2007 | Alessandrini |
| 2009/0002697 A1 | 1/2009 | Freese |
| 2010/0033717 A1 * | 2/2010 | Panza et al. ............... 356/301 |
| 2010/0198080 A1 | 8/2010 | Liu |
| 2010/0245096 A1 | 9/2010 | Jones |
| 2010/0265509 A1 | 10/2010 | Jones |
| 2011/0021908 A1 | 1/2011 | Lee |
| 2011/0104071 A1 | 5/2011 | Lee |
| 2011/0218736 A1 | 9/2011 | Pelletier |
| 2011/0271738 A1 * | 11/2011 | Mcgill et al. ............... 73/23.41 |
| 2012/0018152 A1 | 1/2012 | Zuilekom |
| 2012/0150164 A1 | 6/2012 | Lee |
| 2012/0150451 A1 | 6/2012 | Skinner |
| 2012/0189903 A1 | 7/2012 | Kawada |
| 2012/0211650 A1 | 8/2012 | Jones |
| 2012/0215112 A1 | 8/2012 | Lewis |
| 2012/0229796 A1 * | 9/2012 | Priore ............... 356/51 |
| 2012/0268730 A1 | 10/2012 | Myrick |
| 2012/0279281 A1 | 11/2012 | Myrick |
| 2013/0131517 A1 | 5/2013 | Panasyuk |
| 2013/0201469 A1 * | 8/2013 | Treado et al. ............... 356/39 |
| 2014/0198315 A1 * | 7/2014 | Priore et al. ............... 356/364 |
| 2015/0133751 A1 * | 5/2015 | Stewart et al. ............... 600/310 |

FOREIGN PATENT DOCUMENTS

| | | |
|---|---|---|
| CA | 2765477 | 4/2011 |
| EP | 1212515 | 6/2002 |
| EP | 2087328 | 3/2013 |
| GB | 2390423 | 1/2004 |
| WO | WO0118357 | 3/2001 |
| WO | WO0118357 | 8/2001 |
| WO | WO0235059 | 5/2002 |
| WO | WO2004033841 | 4/2004 |
| WO | WO2007062201 | 5/2007 |
| WO | WO2007062202 | 5/2007 |
| WO | WO2007062224 | 5/2007 |
| WO | WO2007064575 | 6/2007 |
| WO | WO2007064578 | 6/2007 |
| WO | WO2007064579 | 6/2007 |
| WO | WO2008057905 | 5/2008 |
| WO | WO2007084578 | 6/2008 |
| WO | WO2008057095 | 7/2008 |
| WO | WO2008121715 | 10/2008 |
| WO | WO2012108885 | 8/2010 |
| WO | WO2012108886 | 8/2010 |
| WO | WO2010120285 | 10/2010 |
| WO | WO2011049571 | 4/2011 |
| WO | WO2011063086 | 5/2011 |
| WO | WO2012161694 | 11/2012 |
| WO | WO2012166138 | 12/2012 |

OTHER PUBLICATIONS

Chen et al., "Remote Detection of Stress Using Hyperspectral Imaging Technique," ABSTRACT, http://ieeexplore.ieee.org/xpl/login.jsp?tp=&arnumber=5522275&url=http%3A%2F%2Fieeexplore.ieee.org%2Fiel5%2F5510790%2F5522249%2F05522275.pdf%3Farnumber%3D5522275, last accessed Aug. 26, 2013.
Search report, WO2007064578, Mar. 25, 2008.
Search report, WO2008057905, May 9, 2008.

* cited by examiner

SYSTEM AND METHOD FOR ASSESSING TISSUE OXYGENATION USING A CONFORMAL FILTER

RELATED APPLICATIONS

This Application claims priority under 35 U.S.C §119(e) to U.S. Provisional Patent Application No. 61/652,898, entitled "System and Method for Deception Detection Using Hyperspectral Imaging," filed on May 30, 2012. This application is also a continuation-in-part to pending U.S. patent application Ser. No. 13/734,024, filed on Jan. 4, 2013, entitled "Conformal Filter and Method for Use Thereof." These Applications are hereby incorporated by reference in their entireties.

BACKGROUND

Spectroscopic imaging combines digital imaging and optical spectroscopy techniques, which can include Raman scattering, fluorescence, photoluminescence, laser induced breakdown, ultraviolet, visible and infrared absorption spectroscopies. When applied to the chemical analysis of materials, spectroscopic imaging is also referred to as chemical imaging. Instruments for performing spectroscopic (i.e. chemical) imaging typically comprise an illumination source, image gathering optics, focal plane array imaging detectors and imaging spectrometers.

In general, the size or accessibility of a sample determines the choice of image gathering optic. For example, a microscope is typically employed for the analysis of sub-micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, or for objects located at a significant stand-off distance from a sensor, telescopes are appropriate image gathering optics.

Two-dimensional, imaging focal plane array (FPA) detectors are typically employed to detect images formed by the various optical systems. The choice of FPA detector is governed by the spectroscopic technique employed to characterize the sample of interest. For example, silicon (Si) charge-coupled device (CCD) detectors or complementary metal-oxide-semiconductor (CMOS) detectors are typically employed with visible wavelength fluorescence and Raman spectroscopic imaging systems, while indium gallium arsenide (InGaAs) FPA detectors are typically employed with near infrared spectroscopic imaging systems.

Conventional spectroscopic devices operate over a limited range of wavelengths due to the operation ranges of the detectors or imaging spectrometers possible. This enables analysis in the ultraviolet (UV), visible (VIS), near infrared (NIR), short wave infrared (SWIR), mid infrared (MIR), and long wave infrared (LWIR) wavelengths, as well as some overlapping ranges. These correspond to wavelengths of about 180-380 nm (UV), about 380-700 nm (VIS), about 700-2500 nm (NIR), about 850-1700 nm (SWIR), about 700-1700 (VIS-NIR), about 2500-5000 nm (MIR), and about 5000-25000 (LWIR).

Spectroscopic imaging of a sample is commonly implemented by one of two methods. First, point-source illumination can be used on a sample to measure the spectra at each point of the illuminated area. Second, spectra can be collected over the entire area encompassing a sample simultaneously using an electronically tunable optical imaging filter such as an acousto optic tunable filter (AOTF), a multi-conjugate tunable filter (MCF), or a liquid crystal tunable filter (LCTF). Here, the organic material in such optical filters is actively aligned by applied voltages to produce the desired bandpass and transmission function. The spectra obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

Currently, tunable optical filter technology is limited to single bandpass, low throughput operation. Therefore, multiple, discrete bandpass measurements are required for analyte discrimination. The need for multiple measurements translates directly into overall measurement time.

Multivariate Optical Computing (MOC) is an approach which utilizes a compressive sensing device (e.g. an optical computer) to analyze spectroscopic data as it is collected. Other approaches utilize hard coated optical computing filters such as Multivariate Optical Elements (MOEs). MOEs are application-specific optical thin film filters that are used in transmission and reflectance modes. The radiometric response of a MOE-based instrument is proportional to the intended analyte in an associated matrix.

Compressive sensing is a process in which a fully resolved waveform or image is reconstructed from a small set of sparse measurements. A sparse sample implies a waveform or image data set with coefficients close to or equal to zero. Compressive sensing utilizes the redundancy in information across the sampled signal similar to lossy compression algorithms utilized for digital data storage. A fully expanded data set may be created through the solution of an undetermined linear system, an equation where the compressive measurements collected are smaller than the size of the original waveform or image. While compressive sensing holds potential for decreasing measurement time, the use of MOEs have limitations. For example, MOEs are fixed and lack flexibility for adapting to different analytes.

There exists a need for a portable, covert system that can overcome the limitations of the prior art and provide rapid, (i.e. near real-time), reagentless, nondestructive, non-contact tissue oxygenation analysis of biological samples. It would be advantageous if the system could incorporate an adaptable filter that could be used to detect a wide variety of analytes associated with tissue oxygenation while reducing overall measurement time. Such a system could enable the assessment of conditions such as ischemia, viability, and infection, among others.

There also exists a need for a portable system and method capable of linking tissue oxygenation to psychophysiological responses such as deception. Currently, Counter Intelligence (CI) and Human Intelligence (HUMINT) teams utilize deception detection devices that are overt, bulky, obtrusive and relatively slow. Current techniques are further limited by subject movement during the measurement in addition to unfamiliarity with a subject's usual behavior (or baseline). Laser Doppler for pulse rate monitoring is affected by movement of the subject due to the small surface area measured near a subject's carotid artery. Thermal imaging is expensive and requires extensive calibration. Eye monitoring technologies such as blink, pupillometric and eye-tracking imaging require the subject to remain stationary.

A portable, covert sensor would hold potential for determining source truthfulness without physical contact to the subject-of-interest and provide an objective measurement which could be used to augment traditional interrogation and investigation methodologies.

SUMMARY

The present disclosure provides for a portable system and method for standoff analysis of biological tissue samples that can be used to assess tissue oxygenation. By assessing tissue oxygenation, other characteristics including disease and/or psychophysiological responses associated with tissue oxygenation in a subject may be detected. For example, the detection of psychophysiological responses in a subject through the use of visible or short wave infrared (SWIR) techniques. The system and method disclosed herein may hold potential for non-contact measurement of a human subject and for monitoring blood flow or tissue oxygenation, which may be affected by human emotions such as stress. Visible and SWIR techniques may be used in conjunction with at least one other non-contact analytical technique. Examples of such technologies may include thermal imaging, pupillometric imaging or eye-tracking imaging. Therefore, the portable system and method of the present disclosure hold potential for not only assessing biological tissue samples in biomedical applications (such as determining disease and tissue viability), but also in criminal investigations and law enforcement applications for assessing the psychophysiological responses of persons of interest.

The present disclosure provides for a standoff portable system and method incorporating the use of an adaptable tunable filter with the flexibility of conforming to a specific, broadband spectral feature (e.g. pattern or shape). This filter, referred to herein as a "conformal filter," overcomes the limitations of the prior art by simultaneously transmitting multiple passbands that improve discrimination performance for analytes (e.g., discriminating between a target analyte and background), by increasing the throughput of a tunable filter and by increasing the speed of analysis.

In one embodiment, a portable system of the present disclosure may be capable of fusing analytical information from multiple sensors either integrated into the device or as ancillary sensors, resulting in greater deception detection accuracy. Compensation for subject movement during an interrogation will lead to the minimization of false alarms. If covert operation is preferred, a system of the present disclosure may be mounted in a discreet location, as opposed to handheld operation.

In one embodiment, a portable system of the present disclosure may be capable of fusing analytical information from multiple sensors either integrated into the device or as ancillary sensors, resulting in greater detection accuracy. Compensation for subject movement during an interrogation may hold potential for minimization of false alarms. If covert operation is preferred, a portable system of the present disclosure may be mounted in a discreet location, as opposed to handheld operation. The portable system disclosed herein holds potential for a wide variety of applications including biomedical, criminal investigations, immigration control, border security and mass transit security.

A method of the present disclosure provides for illuminating at least a portion of a biological tissue sample to generate a plurality of interacted photons. These interacted photons may be passed through a conformal filter, wherein the conformal filter comprises a tunable filter tuned to a first configuration to filter the interacted photons conforming to a least one spectral shape associated with an analyte of interest. This analyte of interest may be associated with tissue oxygenation. The filtered photons may be detected and at least one test data set may be generated representative of the sample. The test data set may be analyzed to assess at least one characteristic of the biological tissue sample.

The present disclosure also provides for a portable system for assessing a biological tissue sample. The system may comprise at least one collection lens configured to collect a plurality of interacted photons from at least a portion of the biological sample. The system may further comprise a conformal filter configured to enable tuning to a plurality of configurations, wherein each configuration is designed to filter interacted photons conforming to at least one spectral shape associated with an analyte of interest, wherein the analyte is associated with tissue oxygenation. At least one detector may be configured to detect the filtered interacted photons and generate at least one test data set representative of the biological tissue sample.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

FIG. 1A is illustrative of a conformal filter embodiment. FIG. 1B is illustrative of a conformal filter embodiment comprising a rotatable aperture. FIG. 1C is illustrative of a conformal filter embodiment comprising a MCF design.

FIG. 5A illustrates an exemplary experimental set up comprising ammonium nitrate (AN), ammonium sulfate (AS), and urea samples. FIG. 5B illustrates imaging results using a method of the present disclosure. FIG. 5C illustrates detection performance for discriminating between AN and AS.

DETAILED DESCRIPTION

Figure 1A:
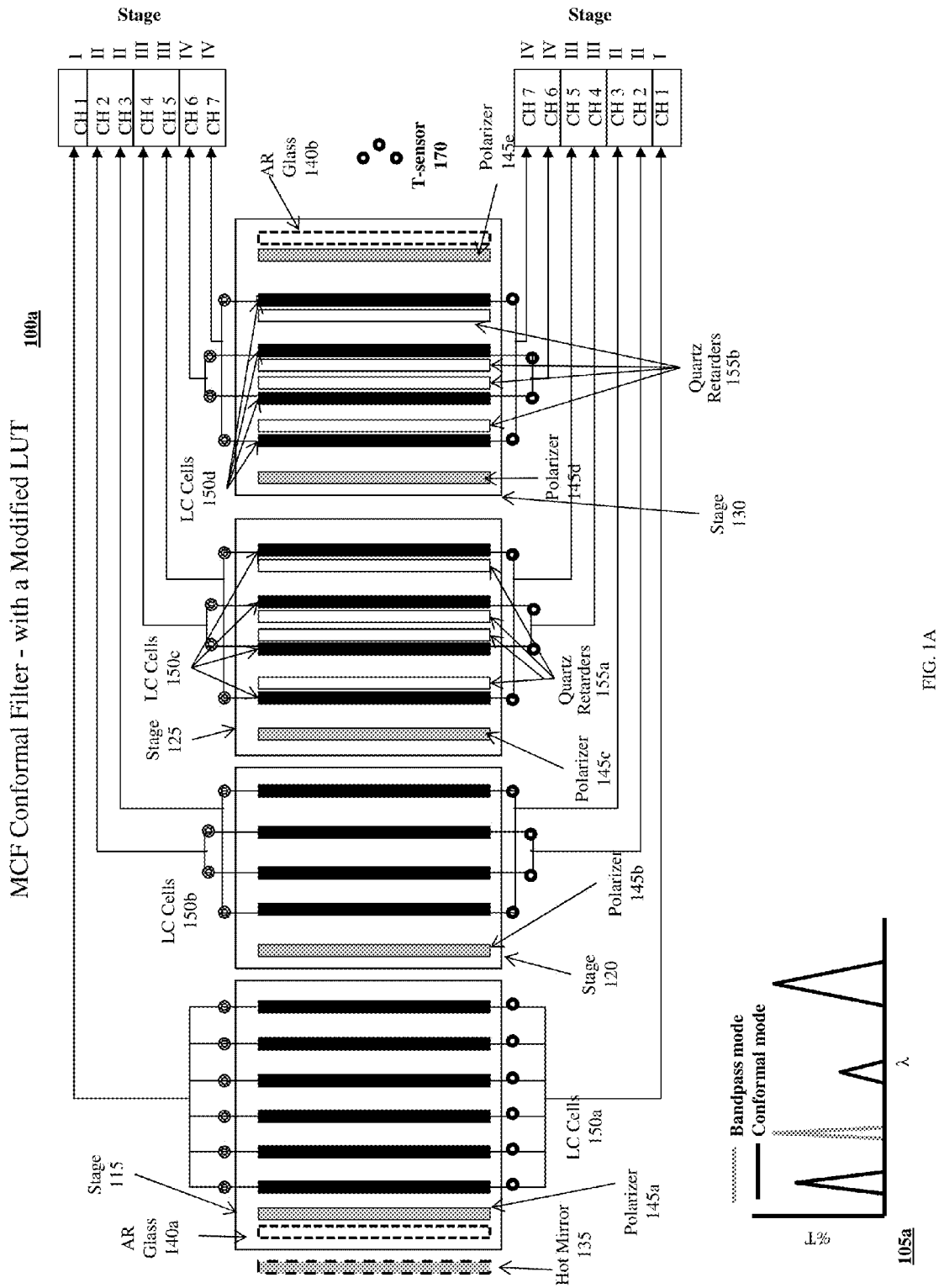
FIGS. 1A-1C are illustrative of exemplary conformal filter embodiments of the present disclosure.

Reference will now be made in detail to the embodiments of the present disclosure, examples of which are illustrated in the accompanying drawings. Wherever possible, the same reference numbers will be used throughout the specification to refer to the same or like parts.

The present disclosure provides for a portable system and method for analyzing a biological tissue sample and detecting analytes associated with tissue oxygenation using a conformal filter. In one embodiment, the present disclosure provides for a system comprising a conformal filter and an associated LUT. The conformal filter may comprise a tunable filter, which is traditionally intended for single bandpass transmission, which is designed to enable tuning to a plurality of different configurations. Each configuration may be designed to filter interacted photons, generated by illuminating a sample, that conform to one or more spectral shapes associated with an analyte of interest. Interacted photons may comprise at least one of the following: photons absorbed by a sample, photons reflected by a sample, photons scattered by a sample, and photons emitted by a sample.

Conformal filter configurations may be determined by consulting the LUT, which corresponds to the analyte. The LUT may comprise at least one voltage associated with each stage of the tunable filter. These voltages may be such that when applied to the associated stage, the tunable filter conforms to a spectral shape associated with the analyte. LUTs may be modified, providing the appropriate conformal filter configurations for detecting a variety of different analytes.

Examples of tunable filters that may be configured for use as a conformal filter may include: a liquid crystal tunable filter, an acousto optical tunable filter, a Lyot liquid crystal tunable filter, an Evans Split-Element liquid crystal tunable filter, a Solc liquid crystal tunable filter, a Ferroelectric liquid crystal tunable filter, Fabry Perot liquid crystal tunable filter, and combinations thereof. In one embodiment, the tunable filter may comprise a MCF. A MCF is an imaging filter with serial stages along an optical signal path in a Solc filter configuration. Angularly distributed retarder elements of equal birefringence are stacked in each stage, with a polarizer between stages. The retarders can include tunable (such as abutted liquid crystals tuned in unison), fixed and/or combined tunable and fixed birefringences. In one embodiment, quartz retarders may be used. Although the retardations are equal within each stage, distinctly different retardations may be used for two or more different stages. This causes some stages to pass narrow bandpass peaks and other stages to have widely spaced bandpass peaks. The transmission functions of the serial stages are superimposed with selected tunable peaks coinciding. The resulting conjugate filter has a high finesse ratio and good out of band rejection.

In one embodiment, the MCF may comprise filter technology available from ChemImage Corporation, Pittsburgh, Pa. This technology is further described in the following U.S. Patents and published U.S. Patent Applications, which are hereby incorporated by reference in their entireties: U.S. Pat. No. 6,992,809, entitled "Multi-Conjugate Liquid Crystal Tunable Filter," U.S. Pat. No. 7,362,489, also entitled "Multi-Conjugate Liquid Crystal Tunable Filter," No. 2012/0300143, entitled "VIS-SNIR Multi-Conjugate Liquid Crystal Tunable Filter," and No. 2011/0279744, entitled "Short Wave Infrared Multi-Conjugate Liquid Crystal Tunable Filter."

Figure 1B:
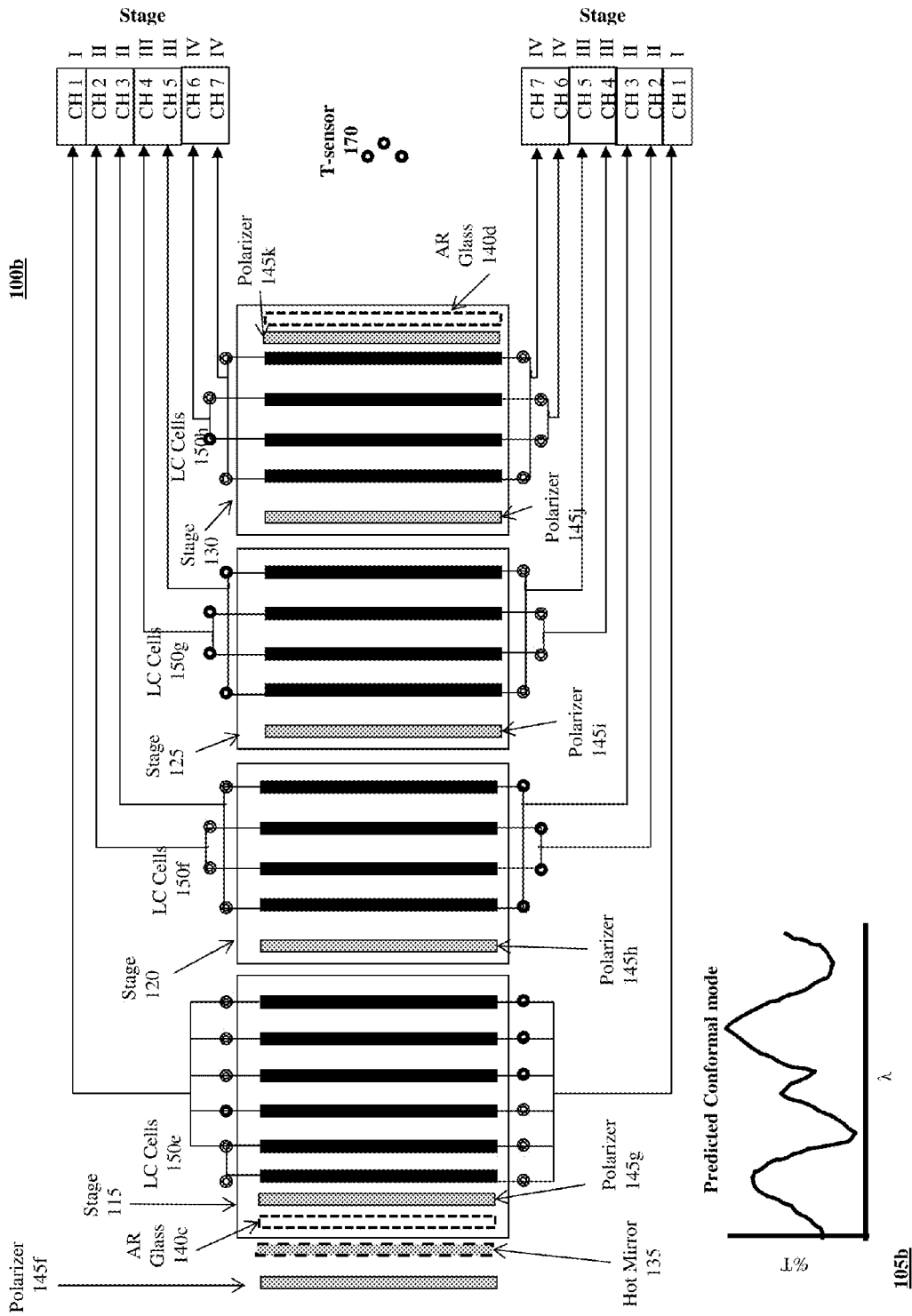
Figure 1C:
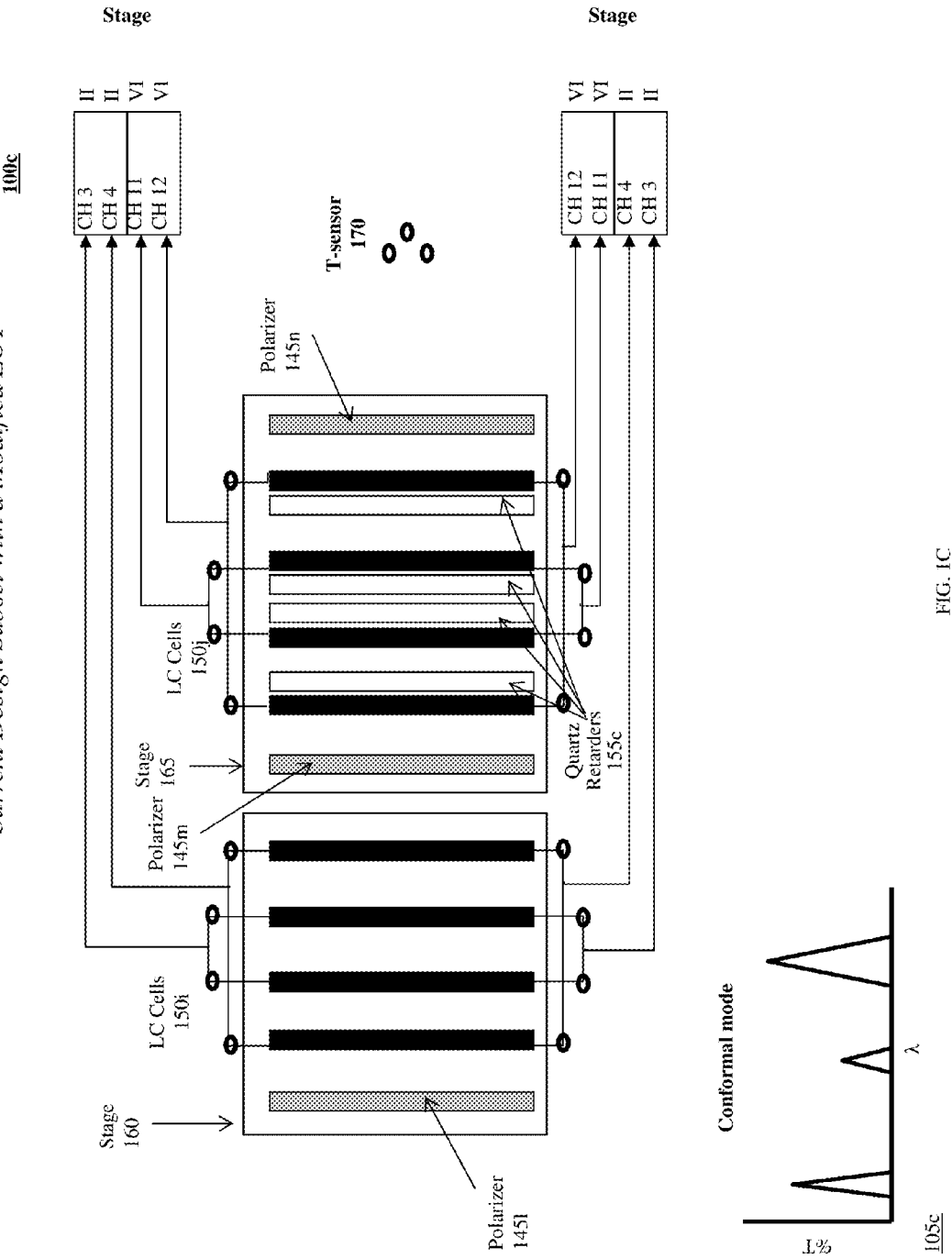

FIGS. 1A-1C illustrate conformal filter embodiments comprising a MCF which may operate in conjunction with one or more LUTs (not illustrated). In FIG. 1A, a hot mirror 135 may be operatively coupled to the MCF. A plurality of filter stages, 115, 120, 125, and 130 may be arranged in a Solc configuration. Each stage may comprise a combination of polarizers 145a-145d, liquid crystal (LC) cells 150a-150d, and quartz retarders 155a-155b. A first antireflective (AR) glass component 140a may be placed in front of the first polarizer 145a and a second AR glass component 140b may be placed after the last polarizer 145e. The filter may be operatively coupled to a temperature sensor 170 for monitoring the temperature of the filter and modifying the LUT as needed for temperature adjustments. Predicted transmission of the filter operating in both a bandpass and a conformal mode is also provided 110.

In FIG. 1B, the MCF 100b may comprise a polarizer 145f operatively coupled to the hot mirror 135 at an input of the MCF. The polarizer may be mounted to a rotatable aperture for increasing optical throughput. In one embodiment, the polarizer 145f may be at least one of the following: a mechanically rotatable polarizer and an electronically tunable LC cell. The polarizer 145f may be tuned as needed each time the MCF is tuned to a new configuration. Filter stages 115, 120, 125, and 130 may further comprise a combination of polarizers 145h-145k and liquid crystal (LC) cells 150e-150h. A first antireflective (AR) glass component 140c may be placed in front of polarizer 145g and a second AR glass component 140d may be placed after the last polarizer 145k. Predicted transmission of the MCF operating in conformal mode is also provided 105b.

In another embodiment, the present disclosure provides for a conformal filter comprising a modified MCF. In such an embodiment, a tunable filter may be modified or specifically designed so that selected individual stages of a traditional tunable filter comprise multiple, lower resolution liquid crystal cells. As illustrated by FIG. 1C, a MCF may be redesigned with fewer stages 160 and 165 for use as a conformal filter 100c. Selected filter stages 160 and 165 may comprise a combination of optical elements including polarizers 145l-145n, LC cells 150i-150j, and quartz retarders 155c. Predicted transmission of the conformal filter is also provided 105c. The present disclosure contemplates that other configurations may be used to modify the MCF and that the present disclosure is not intended to be limited to the design in FIG. 1C. Other conformal filter designs may be selected using a robust, iterative, non-linear optimization methodology. Such a methodology may begin with a random starting configuration and be reconfigured until a minimum response is achieved. The present disclosure contemplates that any iterative, non-linear optimization method known in the art may be applied to design the conformal filter.

Figure 2A:
FIG. 2A is illustrative of a system of the present disclosure.
Figure 2B:
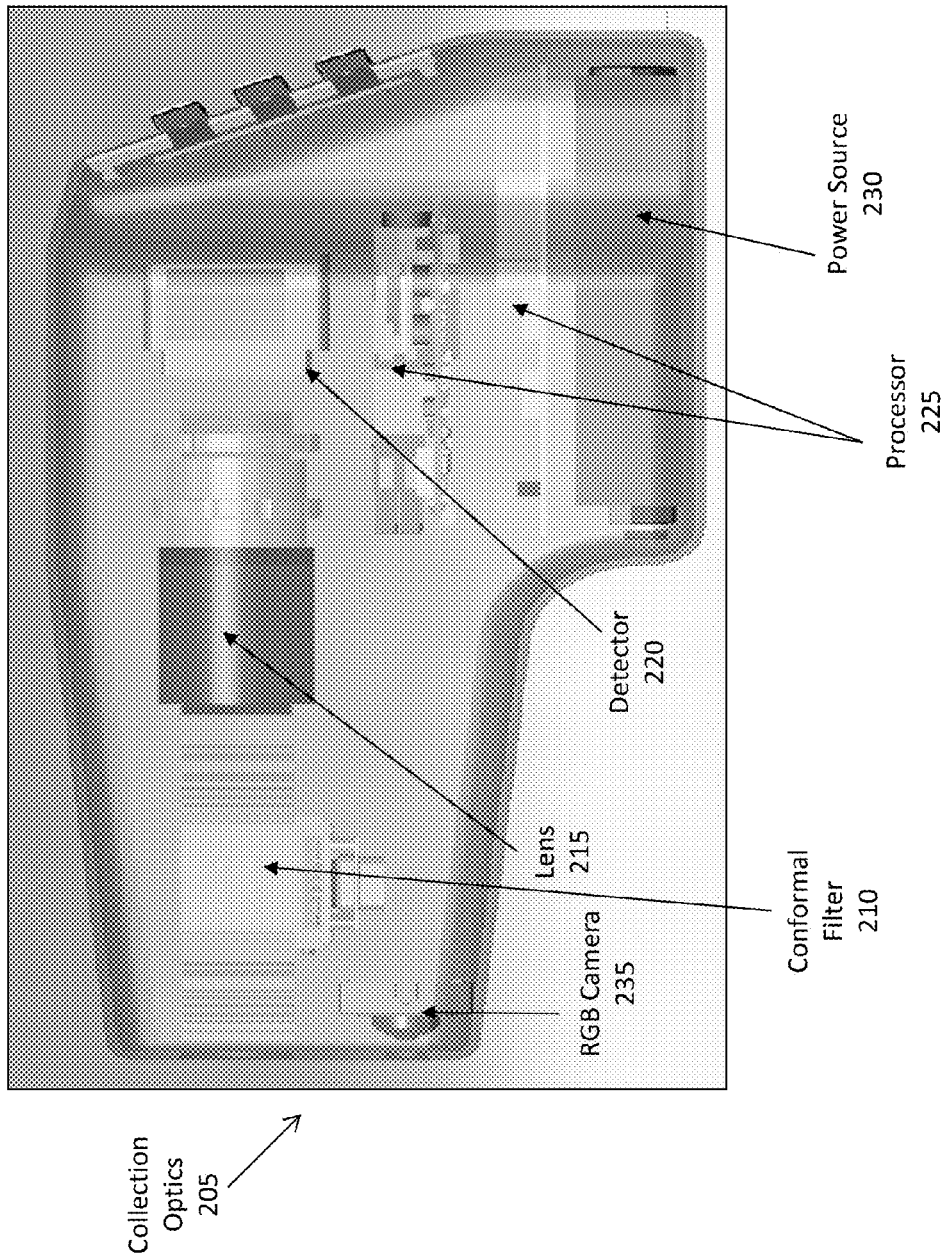
FIG. 2B is illustrative of a system of the present disclosure.

The present disclosure also provides for a portable system comprising a conformal filter. An exemplary housing for the portable system is illustrated in FIG. 2A. FIG. 2B illustrates one embodiment of a portable system 200. The system 200 may comprise at least one collection optics 205 for collecting at least one plurality of interacted photons from a biological tissue sample. These interacted photons may comprise at least one of: photons reflected by the sample, photons absorbed by the sample, photons transmitted by the sample, and photons scattered by the sample. In one embodiment, the system 200 may further comprise at least one illumination source (not illustrated) configured to illuminate the biological tissue sample. The present disclosure contemplates that active and/or passive illumination sources may be used. In one embodiment, a broadband light source may be used. Examples of broadband illumination sources may include, but are not limited to: a quartz tungsten halogen lamp, a high-pressure mercury arc lamp, solar radiation, a light emitting diode, a black-body emitter, and combinations thereof. In an embodiment comprising active illumination, a laser illumination source may be used.

The plurality of interacted photons may be passed through a conformal filter 210. The conformal filter may be configured to enable tuning to a plurality of configurations, wherein each configuration is designed to filter interacted photos conforming to at least one spectral shape associated with an analyte of interest. In one embodiment of the present disclosure, the analyte of interest may be associated with tissue oxygenation.

The filtered photons may then pass through a lens 215 and to a detector 220 to generate at least one test data set. In one embodiment, the detector 220 may be configured to generate at least one of: a visible test data set and a short wave infrared test data set. In one embodiment, the detector 260 may comprise an InGaAs detector, a CCD detector, a CMOS detector, an InSb detector, a MCT detector, and combinations thereof. In one embodiment, the detector 220 may further comprise a focal plane array.

In one embodiment, the portable system 200 may further comprise at least one other detector configured to assess the biological tissue sample using at least one other non-contact analytical technique. Examples of these detectors may include but are not limited to a thermal imager, a pupillometric imager, and an eye tracking imager. In one embodiment, the system may further comprise a RGB camera 235. The RGB camera 235 may be configured to generate at least one RGB image of the biological tissue sample. In one embodiment, the RGB image may be fused with test data generated by utilizing the conformal filter 210.

In one embodiment, the system 200 may further comprise a LUT corresponding to one or more analytes associated with tissue oxygenation. The LUT may comprise at least one voltage associated with each stage of the conformal filter, and each voltage may be configured to cause the tunable filter to conform to a spectral shape associated with the analyte when applied to the associated stage. The system 200 may further comprise one or more processors 225 for operating system components, storing LUTs, and/or storing test data and/or reference data. The processor 225 may further be configured for at least one of: analyzing the test data set, determining at least one psychophysiological response, and configuring the conformal filter. When analyzing the test data set, the processor 225 may be further configured for evaluating the biological tissue sample for at least one of: blood flow, ischemia, infection, oxygenation, and a vascular condition. Examples of vascular conditions may include, but are not limited to: ulcers, peripheral artery disease, wound healing, and tissue viability. The system 200 may further comprise at least one power source 230.

In one embodiment, the system may be configured for use as a handheld device. In another embodiment, the system may be configured for use as a mounted device on a tripod, wall or other surface. The portability of the device holds potential for assessing a sample covertly. For example, the system may be mounted in the same room as the subject or on the opposite side of a one-way mirror. The present disclosure contemplates that the device may be configured to operate at standoff distances of two meters or more.

The present disclosure also contemplates that limitations of the prior art may be overcome by utilizing sensor fusion. In one embodiment, HSI may be used in combination with additional heterogeneous sensors. The result may be a multi-sensor system that can be used in a variety of operations, such as interrogations. Sensor fusion may be utilized to rapidly and accurately assess tissue oxygenation and related characteristics of a sample, such as human deception.

Figure 3:
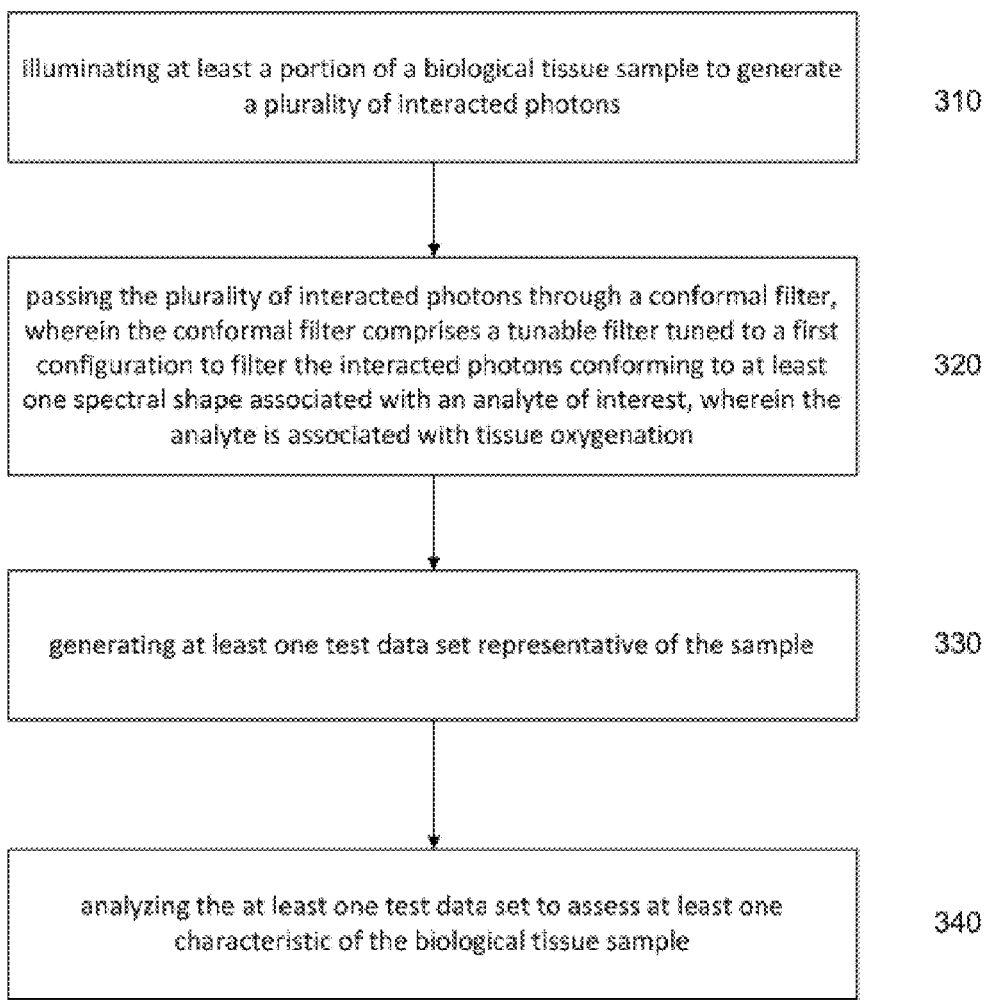
FIG. 3 is representative of a method of the present disclosure.

The present disclosure also provides for a method of assessing biological tissue samples for characteristics of an analyte associated with tissue oxygenation. One embodiment of a method 300 is illustrated by FIG. 3. In step 310 at least a portion of a biological tissue sample may be illuminated to generate a plurality of interacted photons. The present disclosure contemplates that at least one of active illumination and passive illumination may be used to generate the interacted photons. In one embodiment, the sample may be illuminated using wide-field illumination.

In step 320, the interacted photons may be passed through a conformal filter. In one embodiment, the conformal filter comprises a tunable filter tuned to a first configuration to filter the interacted photons conforming to at least one spectral shape associated with an analyte associated with tissue oxygenation. Tunable filter configurations may be determined by searching a LUT associated with the analyte.

At least one test data set representative of the sample may be generated in step 330. In one embodiment, the test data set may comprise at least one of the following: an IR test data set, and a VIS test data set. The IR test data set may comprise a SWIR test data set.

In one embodiment, the at least one test data set may comprise at least one intensity measurement as a function of wavelength. In such an embodiment, utilizing a conformal filter provides for generating a spectral intensity that exploits full spectrum information without the need of generating a full spectrum. In another embodiment, the at least one test data set may comprise at least one spectral image. This spectral image may comprise an image wherein each pixel of the image is the intensity measurement of the analyte of interest at that location. In such an embodiment, utilizing a conformal filter of the present disclosure provides for the generation of a spectral image that exploits hyperspectral information without the need of generating the full hypercube.

The test data set may be analyzed in step 340 to assess at least one characteristic of the biological tissue sample. In one embodiment, analyzing may further comprise determining at least one psychophysiological response. In another embodiment, analyzing may further comprise evaluating at least one of: blood flow, ischemia, infection, oxygenation, and a vascular condition. Examples of vascular conditions may include, but are not limited to: ulcers, peripheral artery disease, wound healing, and tissue viability. In another embodiment, analyzing may further comprise evaluating the biological tissue sample to distinguish between normal and abnormal tissue.

The method 300 may further comprise assessing the biological sample using at least one other non-contact analytical technique. Examples of these techniques may include, but are not limited to: thermal imaging, pupillometric imaging, and eye tracking imaging.

In another embodiment, the method 300 may further comprise generating at least one RGB image of the biological tissue sample. This RGB image may be fused with the test data set to provide both spatial and spectral information about a sample. Additionally, the present disclosure contemplates other data sets may also be generated using other spectroscopic and/or imaging techniques and fused with the test data set and/or the RGB image to provide a fused data set.

In one embodiment, configured to assess psychophysiological responses, an investigator may observe and monitor the level of tissue oxygenation as detected by the device. If the tissue oxygenation rate changes dramatically during the interrogation, software may trigger a notification indicating deception. The present disclosure contemplates that fusion of analytical information from multiple sensors, either integrated into the device or as ancillary sensors, may be used to achieve greater detection accuracy.

The present disclosure contemplates that quantitative and/or qualitative characteristics of a sample may be assessed. Examples of sample characteristics that may be analyzed include, but are not limited to: the presence of the analyte in the sample, the absence of the analyte in the sample, a classification (e.g. class membership) of the analyte, a non-classification of the analyte, a concentration of the analyte, and combinations thereof.

The present disclosure also provides for a method for selecting a conformal filter configuration using an iterative process. This method is referred to herein as Real-time Contrast Enhancement (RtCE) and provides for configurations with high analyte specificity and sensitivity by applying active tunable filter voltage adjustment and feedback from a live measurement scene. Such an approach may be used to calibrate a conformal design for an analyte of interest, refine a previous conformal filter design for an analyte of interest, and/or generate a new conformal filter design for an analyte of interest.

Figure 4:
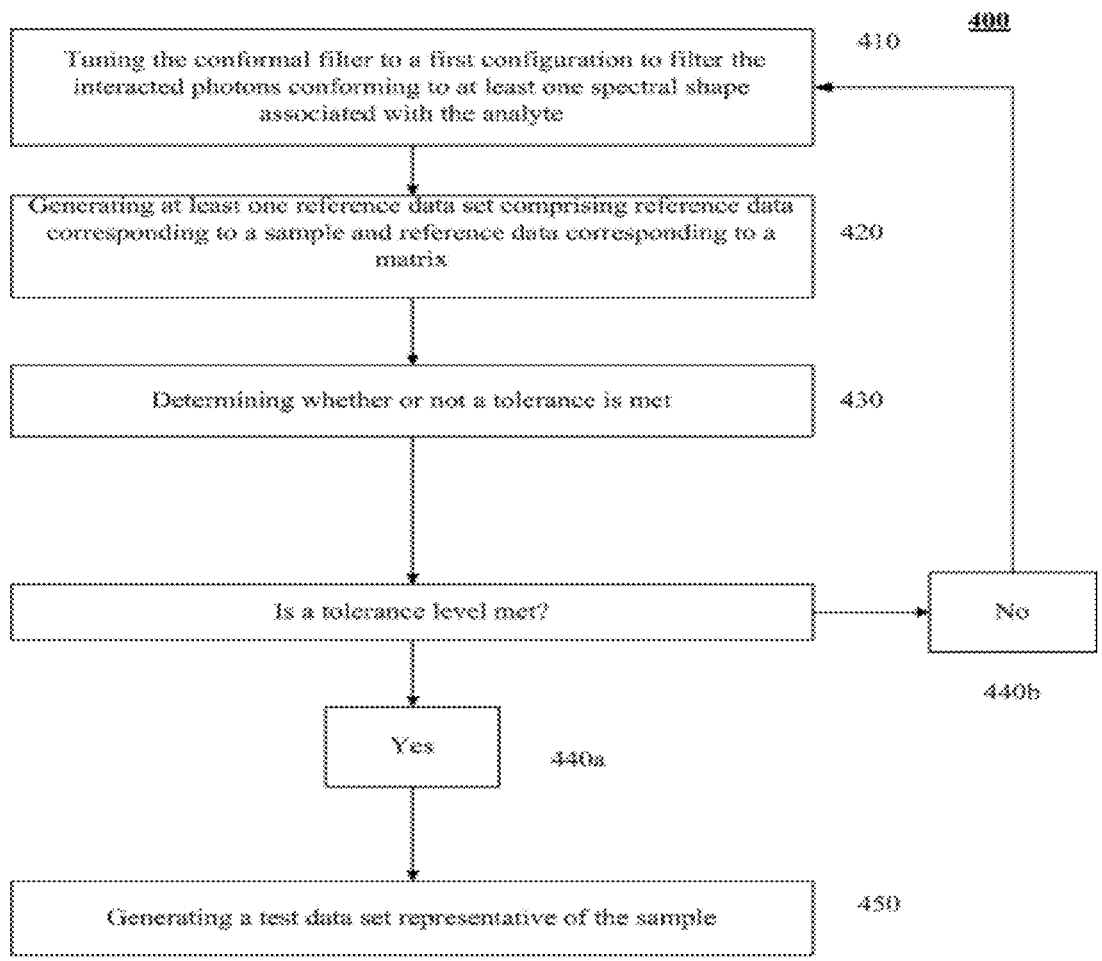
FIG. 4 is representative of a method of the present disclosure.

One embodiment of this optimization process is provided in FIG. 4. The method 400 may comprise tuning a conformal filter to a first configuration to filter interacted photons conforming to at least one spectral shape associated with an analyte associated with tissue oxygenation in step 410. In step 420, at least one reference data set may be generated comprising reference data corresponding to a sample and reference data corresponding to a matrix. In one embodiment, the reference data set may comprise at least one reference spectrum associated with the sample and at least one reference spectrum associated with the matrix.

In another embodiment, the at least one reference data set may comprise at least one reference image comprising the sample and the matrix. A first region of interest may be selected corresponding to the sample and a second region of interest may be selected corresponding to the matrix. Spectral data may be extracted from these regions of interest.

In one embodiment, at least one chemometric technique may be applied to the at least one reference data set (e.g. spectral data). Examples of chemometric techniques include, but are not limited to: correlation analysis, principle component analysis, principle component regression, partial least squares, multivariate curve resolution, Mahalanobis distance, Euclidian distance, band target entropy, band target energy minimization, partial least squares discriminant analysis, adaptive subspace detection, and combinations thereof. Chemometric techniques may be used to compare test data to reference data.

One or more optical computations may also be applied to the test data set. In one embodiment, this optical computation may comprise at least one of the following: $T_1$, $T_1-T_2$, and $(T_1-T_2)/(T_1+T_2)$. Other optical computations known in the art may also be applied and the present disclosure should not be construed as to be limited to those specified herein.

A determination of whether or not a tolerance level is met may be made in step 430. In one embodiment, this determination may comprise applying at least one Figure of Merit (FOM). A FOM is a numerical value that may be used to guide the optimization process. Examples of figures of merit that may be applied include, but are not limited to: Standard error of calibration (SEC), Euclidian Distance, standard error of prediction (SEP), 1-Area Under the Receiver Operator Characteristic Curve (AUROC), optical throughput (% T), and combinations thereof. Other FOMs may be used that incorporate optical throughput, signal to noise ratio (SNR), among others. If a tolerance level is met 440$a$, then a test data set representative of the sample may be generated in step 450. If a tolerance level is not met 440$b$, then the process may be repeated for at least one other conformal filter configuration until a tolerance level is met.

In another embodiment, the present disclosure provides for a portable system comprising a processor and a non-transitory processor-readable storage medium in operable communication with the processor, wherein the storage medium contains one or more programming instructions that, when executed, cause the processor pass at least one plurality of interacted photons generated by a biological tissue sample through a conformal filter, wherein the conformal filter comprises a tunable filter tuned to a first configuration to filter the interacted photons conforming to at least one spectral shape associated with an analyte of interest, wherein the analyte is associated with tissue oxygenation; generate at least one test data set representative of the biological tissue sample; and analyze the test data set to assess at least one characteristic of the biological tissue sample. In one embodiment, the test data set may comprise at least one of: a visible test data set and a short wave infrared test data set.

To analyze the test data set, the storage medium may further comprise programming instructions, that when executed, cause the processor to evaluate the biological tissue sample for at least one of: blood flow, ischemia, infection, oxygenation, and a vascular condition. Examples of vascular conditions include, but are not limited to: ulcers, peripheral artery disease, wound healing, and tissue viability. In one embodiment, the storage medium may further comprise programming instructions, that when executed, cause the portable system to illuminate at least a portion of the biological tissue sample.

The storage medium may further comprise one or more programming instructions, that when executed, cause the processor to assess the biological sample using at least one other non-contact analytical technique. The analytical technique may further comprise at least one of: thermal imaging, pupillometric imaging, and eye tracking imaging. In one embodiment, the storage medium may further comprise programming instructions, that when executed, cause the processor to analyze the test data set to determine at least one psychophysiological response.

In another embodiment, the storage medium may contain one or more programming instructions that, when executed, cause the processor to tune the a conformal filter to a first configuration and filter interacted photons conforming to at least one spectral shape associated with an analyte of interest, generate at least one test data set representative of the biological tissue sample, and analyze the test data set to assess the sample for at least one characteristic of the biological tissue sample. The storage medium may further contain programming instructions that cause the processor to select conformal filter configurations by searching a LUT corresponding to an analyte associated with tissue oxygenation and applying the configuration to the conformal filter.

In another embodiment, the system may further comprise one or more programming instructions that, when executed, cause the processor to iteratively configure the conformal filter until a tolerance level is met. In such an embodiment, the instructions may cause the processor to tune the conformal filter to a first configuration to filter interacted photons conforming to at least one spectral shape associated with the analyte, generate at least one reference data set comprising reference data corresponding to the sample and reference data corresponding to a matrix, and determine whether or not a tolerance level is met. If a tolerance level is met, a test data set may be generated. If a tolerance level is not met, then the steps may be repeated for one or more difference configurations until a tolerance level is met. In one embodiment, whether or not a tolerance level is met may be determined by the processor applying at least one figure of merit. In other embodiments the processor may further analyze the test data set by applying at least one of the following: an optical computation and a chemometric technique.

EXAMPLES

Figure 5A:
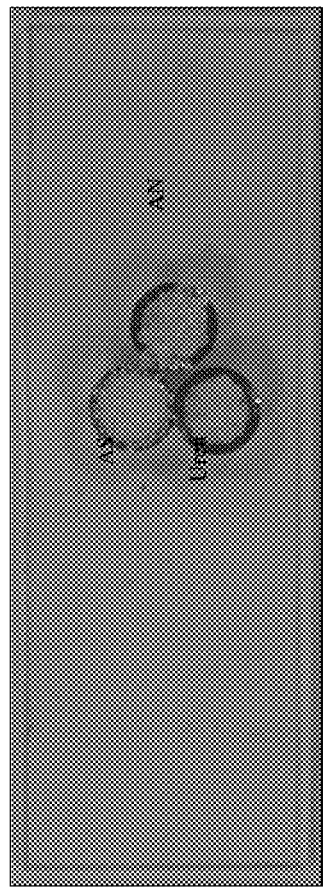
FIGS. 5A-5C are illustrative of the detection capabilities of a conformal filter of the present disclosure.
Figure 5A:
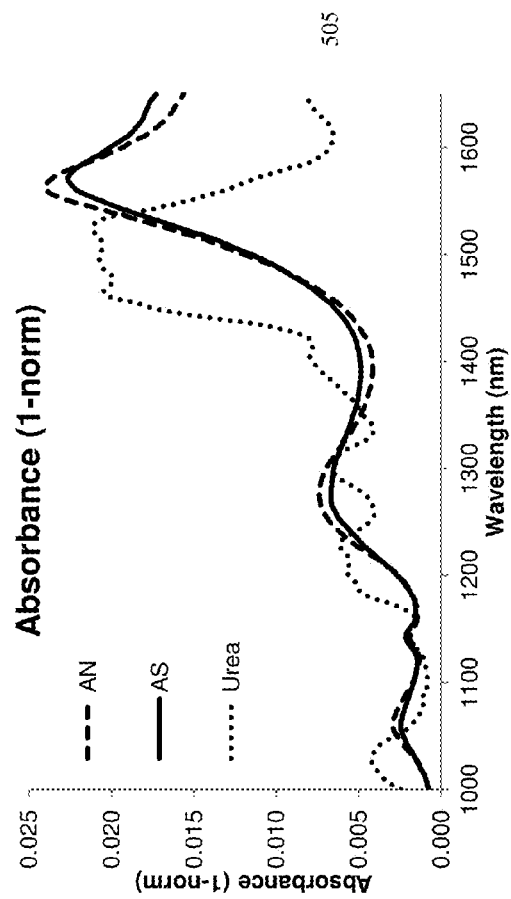
Figure 5B:
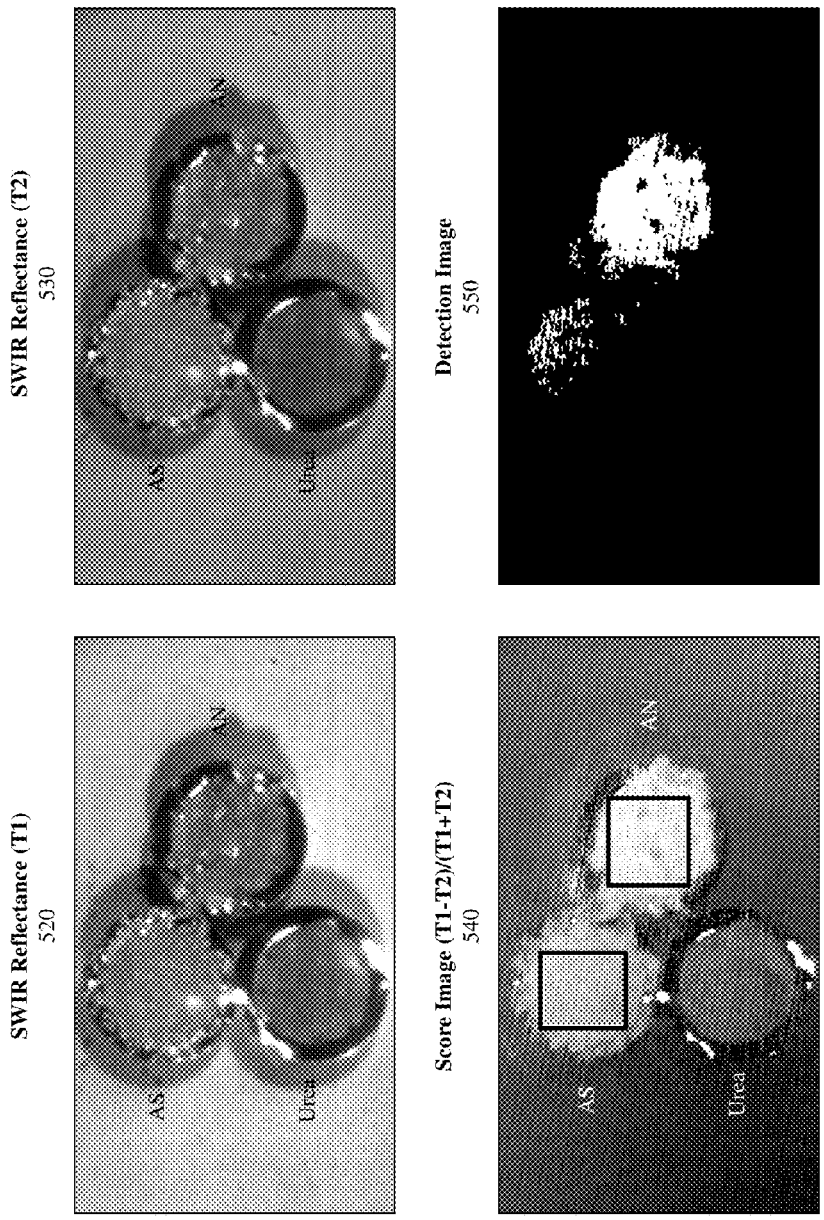
Figure 5C:
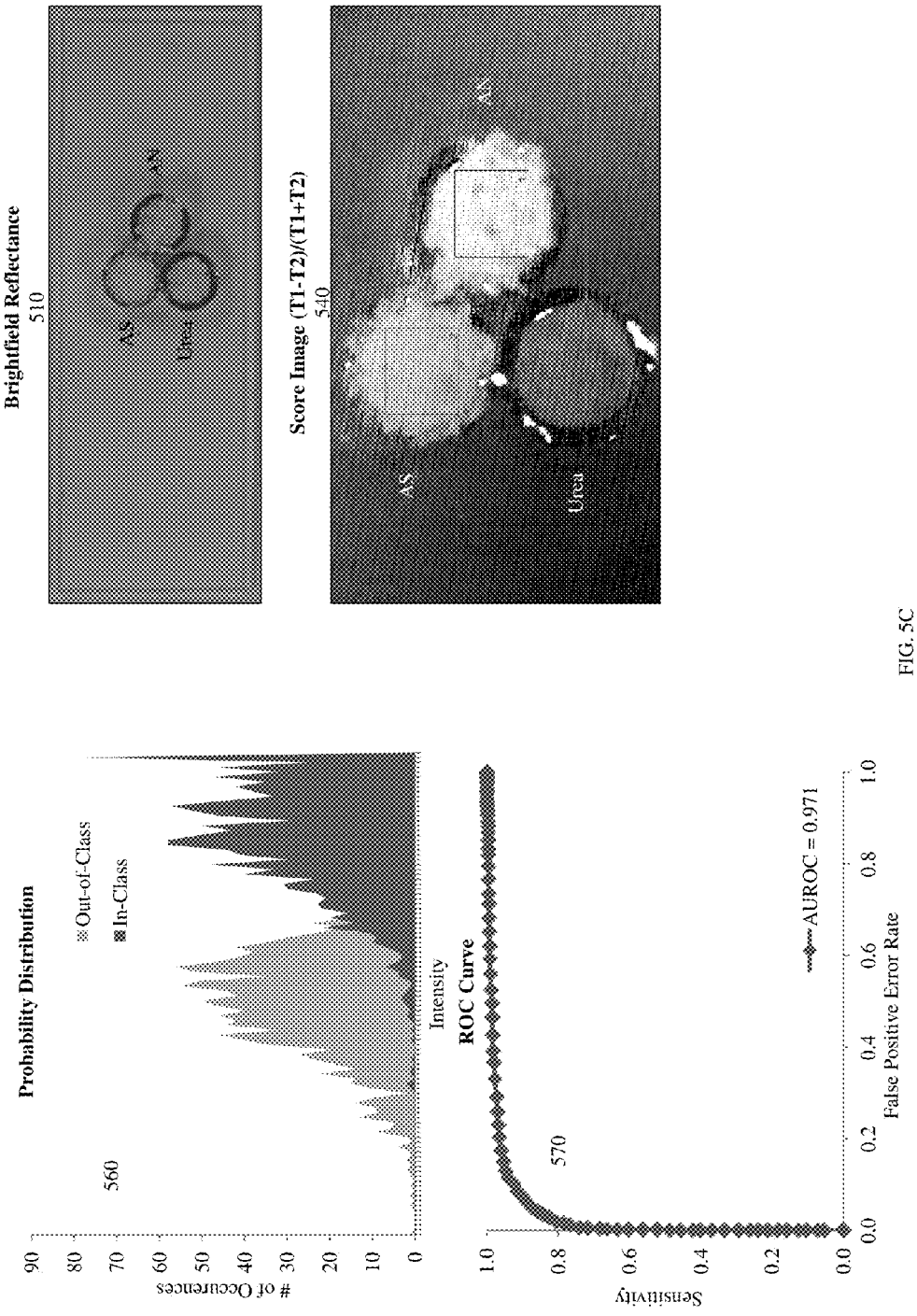

FIGS. 5A-5C are illustrative of the detection capabilities of a conformal filter of the present disclosure. Three samples were prepared comprising AS, AN, and urea. AN was selected as the analyte of interest, AS was selected as a confusant (background), and urea was selected as an interferent. While these samples were used to illustrate detection capabilities of a conformal filter, the present disclosure is not limited to detection of these types of samples and contemplates any analyte of interest may be detected, including those associated with tissue oxygenation. The samples were analyzed using an experimental set up as represented by FIG. 2 wherein the illumination source 210 comprised a quartz tungsten halogen lamp, the conformal filter 250 comprised a MCF, and the detector 260 comprised a SWIR camera. A brightfield reflectance image 510 and a SWIR reflectance image ($T_1$) 530 were generated. Spectral data for each substance 505 is also illustrated in FIG. 5A.

FIG. 5B illustrates the detection capabilities of the present disclosure when an RtCE methodology is applied. A second SWIR reflectance image ($T_2$) was generated 530. The optical computation ($T_1-T_2$)/($T_1+T_2$) was applied, and a score image 540 was generated. As can be seen from the detection image 550, AN was easily detected and distinguished from AS and urea. FIG. 5C is illustrative of the detection results after applying additional processing steps such as contrast flip and saturation removal. A probability distribution 560, from the score image 540, illustrates in-class v. out-of-class detections. The ROC curve 570 illustrates the sensitivity and false positive results achieved and was generated by applying a threshold to the probability distribution 560. As illustrated by the Examples, the system and method of the present disclosure hold potential for detecting analytes and discriminating between "near neighbors," i.e., analytes with similar spectral features.

Figure 6:
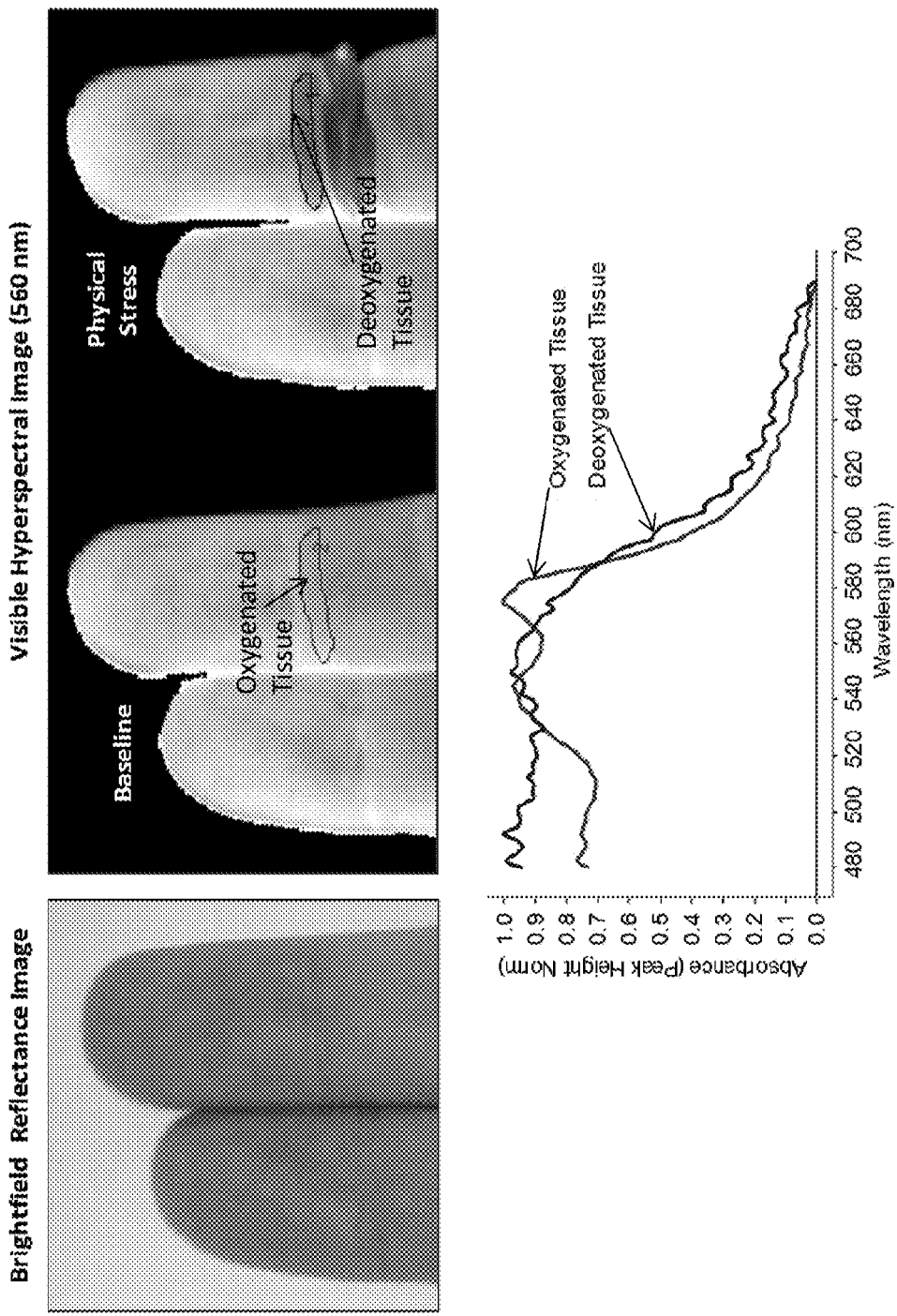
FIG. 6 is representative of the detection capabilities of tissue oxygenation.

FIG. 6 is provided to illustrate detection capabilities of tissue oxygenation using traditional hyperspectral imaging. As illustrated in the Figure, visible spectroscopic differences may be observed in human tissue undergoing stress or strain. The Figure illustrates an example of the difference in tissue oxygenation between an unperturbed finger and a finger undergoing physical restriction. Upon blood flow restriction applied to the finger, a localized concentration of deoxygenated blood occurs near the perturbation site. The difference between the deoxygenated and oxygenated blood is observed as a visible spectroscopic difference near 560 nm as a single peak as opposed to the doublet observed for oxygenated blood.

The present disclosure contemplates the fusion of two or more different sensors. To achieve sensor fusion, one or more additional sensors may be operatively coupled to the device. Examples of these other sensors may include: thermal imaging sensors, pupillometric imaging sensors or eye-tracking imaging sensors. Compensation for subject movement during an interrogation holds potential for minimizing false alarms. The system may also be connected to wireless networks, facilitating the ease of disseminating pertinent data to applicable local computer networks.

Figure 7:
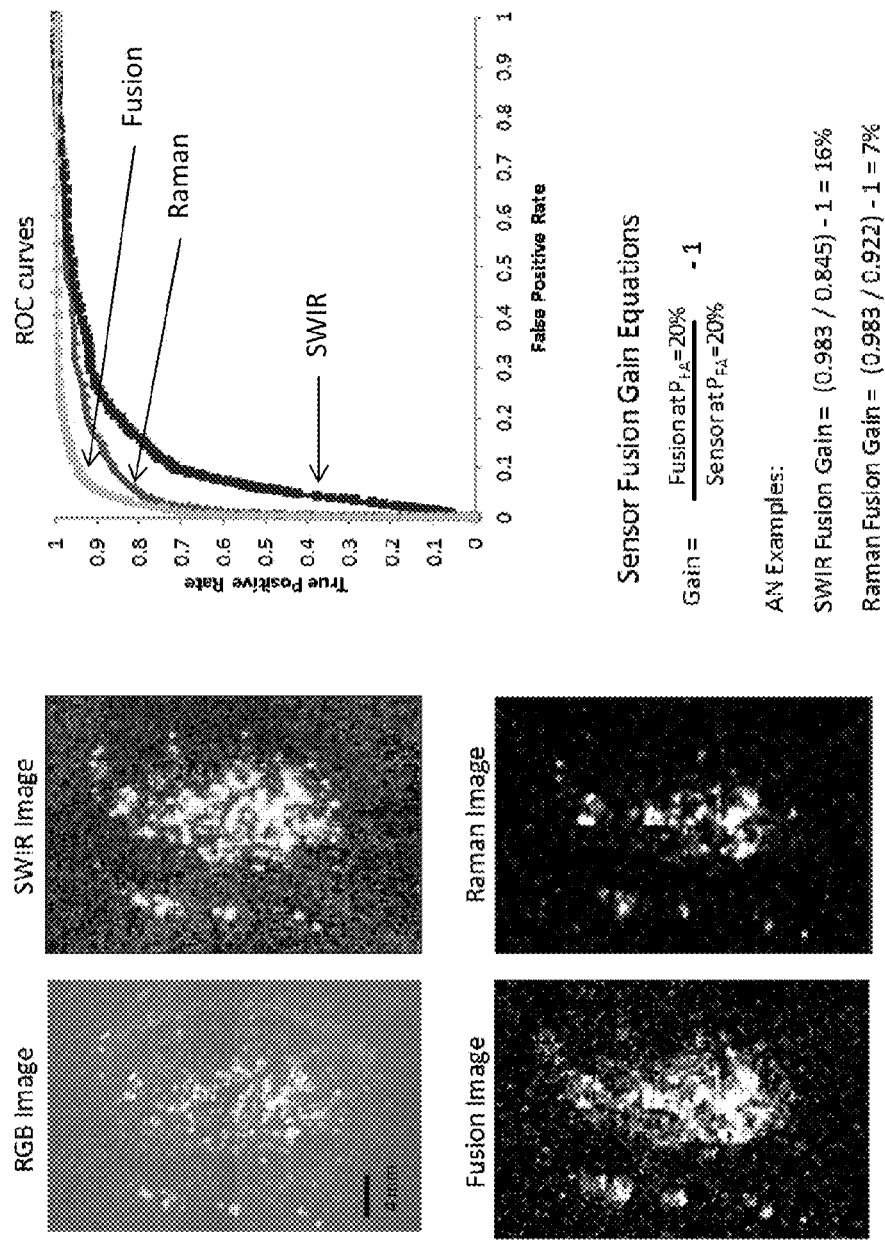
FIG. 7 is representative of the detection capabilities of the present disclosure using sensor fusion.

An example of demonstrated sensor fusion gain is illustrated in FIG. 7. As can be seen in the Figure, the combination of Raman HSI and SWIR HSI yields a superior Receiver Operator Characteristic (ROC) curve performance than each individual sensor. Therefore, the fusion of these techniques holds potential for increasing detection capabilities.

There are different levels of sensor fusion, and embodiments of the present disclosure may incorporate multiple levels. Data level sensor fusion is the combination of unprocessed sensor data. A feature vector is generated from the signals, and a classifier is used to map the feature vector into scores, or measure of similarity with vectors associated with targets and background used for training.

Feature level sensor fusion is the combination of feature vectors extracted from the different sensor data which represent object properties such as color, reflectivity, light polarizing properties, or temperature. Algorithms map instrument signals in sensor outputs, so individual instruments, or instruments in combination, can perform the duties of multiple sensors. An advantage of feature level sensor fusion is the incorporation of physical models and expert knowledge into the context of the measurement. Sensor output signals are computed and incorporated into the sensing process because they are expected to be sensitive to specific features associated with targets of interest. Again, a classifier is used to map feature vectors into scores, or measure the similarity with vectors associated with targets and background used for training.

To perform decision level sensor fusion each sensor is queried for its estimate of the presence of the target object (e.g. disturbed earth or buried device). The estimates can be combined using several methods including Naïve Bayes' approaches, Dempster-Shafer theory, fuzzy probabilities, rule based methods, voting techniques, Stacked Generalization and Adaboost.

While the disclosure has been described in detail in reference to specific embodiments thereof, it will be apparent to one skilled in the art that various changes and modifications can be made therein without departing from the spirit and scope of the embodiments. Additionally, while the examples provided herein related to specific analytes, the present disclosure is not limited to these analytes and may be used to detect a wide variety of analytes of interest. Thus, it is intended that the present disclosure cover the modifications and variations of this disclosure provided they come within the scope of the appended claims and their equivalents.

What is claimed is:

1. A method comprising:
   illuminating at least a portion of a biological tissue sample to generate a plurality of interacted photons;
   passing the plurality of interacted photons through a conformal filter having a plurality of filter stages, wherein each stage comprises a tunable filter and at least one associated voltage;
   tuning the plurality of filter stages to a first configuration to filter the interacted photons conforming to at least one spectral shape associated with an analyte of interest is associated with tissue oxygenation;
   generating at least one test data set representative of the sample; and
   analyzing the at least one test data set to assess at least one characteristic of the biological tissue sample.

2. The method of claim 1, wherein the at least one characteristic is selected from the group consisting of the presence of the analyte, the absence of the analyte, and a concentration of the analyte.

3. The method of claim 1, wherein the at least one test data set is selected from the group consisting of a spectral intensity of the sample and a spectral image representative of the sample.

4. The method of claim 1, wherein the illuminating is selected from the group consisting of active illumination and passive illumination.

5. The method of claim 1, wherein the illuminating comprises wide field illumination.

6. The method of claim 1, wherein the at least one characteristic comprises a psychophysiological response.

7. The method of claim 1 further comprising assessing the biological sample using at least one other non-contact analytical technique.

8. The method of claim 7, wherein the analytical technique is selected from the group consisting of thermal imaging, pupillometric imaging, and eye tracking imaging.

9. The method of claim 1, wherein the at least one characteristic comprises a vascular condition of the biological tissue sample.

10. The method of claim 9, wherein the vascular condition is selected from the group consisting of ulcers, peripheral artery disease, wound healing, and tissue viability.

11. The method of claim 1, wherein the at least one characteristic is selected from the group consisting of blood flow, ischemia, infection, and oxygenation.

12. The method of claim 1, further comprising analyzing the biological tissue sample to distinguish between normal and abnormal tissue.

13. The method of claim 1, wherein the analyzing further comprises applying at least one optical computation to the at least one test data set.

14. The method of claim 13, further comprising generating a first reflectance image (T1) and second reflectance image (T2) and wherein the optical computation further comprises one or more of T1, T1−T2, and (T1−T2)/(T1+T2).

15. The method of claim 1 further comprising generating at least one RGB image representative of the biological tissue sample.

16. The method of claim 15 further comprising fusing the RGB image and the test data set.

17. The method of claim 1, wherein the test data comprises one or more of a visible test data set and a short wave infrared test data set.

18. A portable system comprising:
a collection lens configured to collect a plurality of interacted photons from at least a portion of a biological tissue sample;
a conformal filter having a plurality of filter stages wherein each filter stage comprises a tunable filter and at least one associated voltage, the conformal filter being configured to enable tuning to a plurality of configurations, wherein each configuration is designed to filter interacted photons to generate filtered interacted photons conforming to at least one spectral shape associated with an analyte of interest associated with tissue oxygenation; and
a first detector configured to detect the filtered interacted photons and generate a test data set representative of the biological tissue sample.

19. The portable system of claim 18, further comprising an RGB camera configured to generate an image of the biological tissue sample.

20. The portable system of claim 18, further comprising an illumination source configured to illuminate the biological tissue sample and generate the first plurality of interacted photons.

21. The portable system of claim 20, wherein the illumination source comprises one or more of an active illumination source and a passive illumination source.

22. The portable system of claim 18 further comprising a look-up table corresponding to the analyte, wherein the look-up table comprises at least one voltage associated with each of the plurality of filter stages, and wherein each voltage is configured to cause the tunable filter in each filter stage to conform to a spectral shape associated with the analyte when applied to the associated stage.

23. The portable system of claim 18, wherein the tunable filter is selected from the group consisting of a liquid crystal tunable filter, a multi-conjugate tunable filter, an acusto optical tunable filter, a Lyot liquid crystal tunable filter, an Evans Split-Element liquid crystal tunable filter, a Solc liquid crystal tunable filter, and a Ferroelectric liquid crystal tunable filter.

24. The portable system of claim 18, wherein the first detector is selected from the group consisting of an InGaAs detector, a CCD detector, a CMOS detector, an InSb detector, and a MCT detector.

25. The portable device of claim 18, wherein the first detector further comprises a focal plane array.

26. The portable system of claim 18, wherein the illumination source comprises a broadband light source.

27. The portable system of claim 18, wherein the illumination source is selected from the group consisting of a quartz tungsten halogen lamp, a high-pressure mercury arc lamp, solar radiation, a light emitting diode, and a blackbody emitter.

28. The portable system of claim 27, further comprising a second detector configured to assess the biological sample using a non-contact analytical technique.

29. The portable system of claim 28, wherein the analytical technique is selected from the group consisting of thermal imaging, pupillometric imaging, and eye tracking imaging.

30. The portable system of claim 18, further comprising a processor configured to perform one or more of an analysis of the test data set, a determination of at least one psychophysiological response, and a configuration of the conformal filter.

31. The portable system of claim 30, wherein analyzing comprises evaluating the biological tissue sample for one or more of blood flow, ischemia, infection, and oxygenation.

32. The portable system of claim 18, wherein analyzing comprises evaluating a vascular condition of the biological tissue sample.

33. The portable system of claim 32, wherein the vascular condition is selected from the group consisting of an ulcer, a peripheral artery disease, a wound healing, and a tissue viability.

34. The portable system of claim 18, wherein the test data set further comprises one or more of a visible test data set and a short wave infrared test data set.

35. The portable system of claim 18, wherein analyzing comprises evaluating the biological tissue sample to distinguish between normal and abnormal tissue.

36. A portable system comprising:
a processor; and
a non-transitory processor-readable storage medium in operable communication with the processor, wherein the storage medium contains one or more programming instructions that, when executed, cause the processor to perform the following:
cause a conformal filer to filter interacted photons generated by a biological tissue sample, wherein the conformal filter comprises a plurality of filter stages wherein each filter stage comprises a tunable filter and at least one associated voltage to configure the conformal filter to a first configuration to filter the interacted photons conforming to at least one spectral shape associated with an analyte of interest associated with tissue oxygenation;
generate a test data set representative of the biological tissue sample; and
analyze the test data set to assess a characteristic of the biological tissue sample.

37. The portable system of claim 36, wherein the storage medium further contains one or more programming instructions, that when executed, cause the portable system to illuminate the biological tissue sample to generate the plurality of interacted photons.

38. The portable system of claim 36, wherein the storage medium further contains one or more programming instructions, that when executed, cause the processor to further assess the biological sample using at least one other non-contact analytical technique.

39. The portable system of claim 38, wherein the analytical technique comprises one or more of thermal imaging, pupillometric imaging, and eye tracking imaging.

40. The portable system of claim 36, wherein the storage medium further contains one or more programming instructions, that when executed, cause the processor to analyze the test data set to determine at least one psychophysiological response.

41. The portable system of claim 36, wherein the storage medium further contains one or more programming instructions, that when executed to analyze the test data set, further cause the processor to evaluate the biological tissue sample to perform one or more of distinguishing between normal and abnormal tissue, determine blood flow, identify ischemia, identify an infection, and determine oxygenation.

42. The portable system of claim 36, wherein the storage medium further contains one or more programming instructions, that when executed to analyze the test data set, further cause the processor to evaluate at least one vascular condition of the biological tissue sample.

43. The portable system of claim 42, wherein the storage medium further contains one or more programming instructions, that when executed to evaluate at least one vascular condition of the biological tissue sample further cause the processor to evaluate one or more of an ulcer, a peripheral artery disease, a wound healing, and a tissue viability.

44. The portable system of claim 36, wherein the storage medium further contains one or more programming instructions, that when executed to generate the test data set, further cause the processor to generate one or more of a visible test data set and a short wave infrared test data set.

* * * * *